(12) United States Patent
Fazzi et al.

(10) Patent No.: US 11,202,678 B2
(45) Date of Patent: Dec. 21, 2021

(54) ELECTROMAGNETIC TRACKING WITH WIRELESS DETACHABLE PROCESSING DEVICE

(71) Applicant: KONINKLIJKE PHILIPS N.V., Eindhoven (NL)

(72) Inventors: Alberto Fazzi, Eindhoven (NL); Maurice Alain Termeer, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 524 days.

(21) Appl. No.: 15/578,970

(22) PCT Filed: Jun. 10, 2016

(86) PCT No.: PCT/EP2016/063388
§ 371 (c)(1),
(2) Date: Dec. 1, 2017

(87) PCT Pub. No.: WO2016/198661
PCT Pub. Date: Dec. 15, 2016

(65) Prior Publication Data
US 2018/0132945 A1    May 17, 2018

(30) Foreign Application Priority Data
Jun. 12, 2015   (EP) .................................... 15171774

(51) Int. Cl.
*A61B 34/20*    (2016.01)
*A61B 8/00*    (2006.01)
(Continued)

(52) U.S. Cl.
CPC .............. *A61B 34/20* (2016.02); *A61B 5/061* (2013.01); *A61B 5/062* (2013.01); *A61B 8/12* (2013.01);
(Continued)

(58) Field of Classification Search
CPC ........... A61B 2017/00221; A61B 2017/00411; A61B 2034/2051; A61B 2560/045;
(Continued)

(56) References Cited

U.S. PATENT DOCUMENTS

| 7,729,742 B2 | 6/2010 | Govari | |
| 2003/0120150 A1* | 6/2003 | Govari | ................. A61B 5/0031 600/424 |

(Continued)

FOREIGN PATENT DOCUMENTS

| CN | 101553159 A | * 10/2009 | ........... G01D 5/2086 |
| WO | 2008132657 A1 | 11/2008 | |

(Continued)

Primary Examiner — Amanda Lauritzen Moher

(57) ABSTRACT

The present invention relates to electromagnetic tracking of medical devices. In order to provide improved tracking of medical devices, a wireless readout unit (10) for an electromagnetic tracking system of medical devices is provided. The wireless readout unit comprises a data input (12), a data processor (14) and a data output (16). The data input is configured to receive raw signals (18) from an electromagnetic sensor, and the data processor is configured to at least partly pre-process the raw signals provided by the data input for further transformation. Further, the data output is configured for data transmission of the at least partly pre-processed data to a control unit of an electromagnetic tracking system of medical devices. The data output provides a wireless data link (20) to a control unit.

13 Claims, 3 Drawing Sheets

(51) Int. Cl.
*A61B 5/06* (2006.01)
*A61B 8/12* (2006.01)
*A61B 90/98* (2016.01)
*A61B 8/08* (2006.01)
*A61B 17/00* (2006.01)

(52) U.S. Cl.
CPC ............ *A61B 8/4254* (2013.01); *A61B 90/98* (2016.02); *A61B 8/0883* (2013.01); *A61B 2017/00221* (2013.01); *A61B 2017/00411* (2013.01); *A61B 2034/2051* (2016.02); *A61B 2560/045* (2013.01)

(58) Field of Classification Search
CPC ......... A61B 34/20; A61B 5/061; A61B 5/062; A61B 8/0883; A61B 8/12; A61B 8/4254; A61B 90/98
See application file for complete search history.

(56) References Cited

U.S. PATENT DOCUMENTS

| | | | | |
|---|---|---|---|---|
| 2004/0011365 | A1* | 1/2004 | Govari | A61B 17/1707 128/899 |
| 2005/0104776 | A1* | 5/2005 | Anderson | A61B 5/06 342/450 |
| 2007/0265583 | A1 | 11/2007 | Secora | |
| 2007/0265690 | A1 | 11/2007 | Lichtenstein | |
| 2008/0097475 | A1 | 4/2008 | Jaggi | |
| 2009/0085559 | A1* | 4/2009 | Anderson | A61B 5/062 324/207.22 |
| 2010/0056871 | A1 | 3/2010 | Govari et al. | |
| 2011/0015533 | A1* | 1/2011 | Cox | A61B 5/283 600/509 |
| 2012/0226148 | A1 | 9/2012 | Jaggi et al. | |
| 2014/0273631 | A1 | 9/2014 | Birchard | |
| 2016/0029995 | A1* | 2/2016 | Navratil | A61B 5/08 600/301 |
| 2018/0279996 | A1* | 10/2018 | Cox | A61B 8/488 |

FOREIGN PATENT DOCUMENTS

| | | | | |
|---|---|---|---|---|
| WO | 20102088535 | A1 | 6/2012 | |
| WO | 2012173697 | A1 | 12/2012 | |
| WO | WO 2014/152260 | * | 9/2014 | ............... A61B 5/08 |

* cited by examiner

ELECTROMAGNETIC TRACKING WITH WIRELESS DETACHABLE PROCESSING DEVICE

CROSS-REFERENCE TO PRIOR APPLICATIONS

This application is the U.S. National Phase application under 35 U.S.C. § 371 of International Application Serial No. PCT/EP2016/063388, filed on Jun. 10, 2016, which claims the benefit of European Patent Application No. 15171774.1, filed on Jun. 12, 2015. This application is hereby incorporated by reference herein.

FIELD OF THE INVENTION

The present invention relates to electromagnetic tracking of medical devices, and relates in particular to a wireless readout unit for an electromagnetic tracking system of medical devices, to a medical device for electromagnetic tracking, to an electromagnetic tracking system of medical devices and to a method for tracking of medical devices.

BACKGROUND OF THE INVENTION

Electromagnetic tracking is used, for example, in certain interventional procedures in order to track devices, e.g. their position and orientation, that are used during the procedures. As an example, a wire connection may be provided to connect an electromagnetic sensor to a computation unit of an electromagnetic tracking system. As a further example, US 2010/0056871 A1 describes the synchronization of medical devices via a digital interface. For example, a cardiac catheterization system is described including two catheters. The catheters comprise a wireless digital interface, which communicates with a corresponding interface in a console. The respective counterpart, i.e. the interface in the console, communicates with a central processing unit that receives and processes the data signals conveyed from the two catheters. The catheters may be provided with a position sensor generating signals that are indicative of the position coordinates, for which the position sensors can sense magnetic fields generated by a field generator.

SUMMARY OF THE INVENTION

There may be a need to further improve the tracking of medical devices.

The object of the present invention is solved by the subject-matter of the independent claims, wherein further embodiments are incorporated in the dependent claims.

According to a first aspect, a wireless readout unit for an electromagnetic tracking system of medical devices is provided. The wireless readout unit comprises a data input, a data processor and a data output. The data input is configured to receive raw signals from an electromagnetic sensor. The data processor is configured to at least partly pre-process the raw signals provided by the data input for further transformation. The data output is configured for data transmission of the at least partly pre-processed data to a control unit of an electromagnetic tracking system of medical devices. The data output provides a wireless data link to a control unit. For the pre-processing of the raw signals the data processor is configured to perform identification and/or separation of different signal components induced by different field emitting elements of the field generator, and/or extraction of signal components or signal parameters used for triangulation.

Advantageously, the wireless readout unit enables to further improve the wireless data link due to the pre-processing of the raw signals. In other words, the stream of raw sensor signals is not continuously transferred via the data link to the control unit, but the raw signals are pre-processed and then transferred, and hence a reduction of the data stream, or a partition of the data stream, is enabled, which means an improvement in view of the wireless data link. Hence, also the overall situation in an operational theatre can be improved, since there may be a large number of devices that are connected to the tracking system or that communicate with each other via wireless data links. The pre-processing also makes the communication more reliable.

In an example, the control unit is a processing unit, or computation unit or console of an electromagnetic tracking system.

According to an example, for the pre-processing of the raw signals, the data processor is further configured to perform at least one of the following: filter of the raw signals, amplification of the raw signals, analogue processing and A/D (analogue-to-digital) conversion of the signals.

In an example, for the pre-processing of the raw signals, the data processor is configured to perform an identification of an electromagnetic source of a field generator.

In an example, the data processor is configured to perform calculation of signal parameters that can be used for triangulation of the sensor position.

According to an example, the wireless readout unit is provided as a detachable dongle to be temporarily attached to a medical device.

Advantageously, the wireless readout unit can be temporarily mounted to a number of different medical devices. Hence, a tracking of a number of medical devices that may be used during an interventional procedure for example, can be tracked, while reducing the number of the wireless readout units to a minimum, since a single dongle can be used for a plurality of devices. Hence, in order to track all the devices that will be used during a particular intervention, the devices can be chosen from a larger number of devices, and the chosen devices may be equipped with the (detachable) wireless readout unit. For example, the devices as such may be disposable, and the (detachable) wireless readout unit is used at least a number of times.

According to a second aspect, a medical device for electromagnetic tracking is provided. The device comprises at least a body portion, an electromagnetic tracking sensor and a wireless readout unit. The wireless readout unit is provided according to one of the above-mentioned examples. The electromagnetic tracking sensor is configured to measure an intensity of an electromagnetic field generated by a field generator. The electromagnetic tracking sensor is fixedly attached to a determined part of the medical device. The wireless readout unit is at least temporarily attached to the body portion.

The medical device may be provided for a particular interventional purpose, for example to be used during an interventional procedure. The device is hence a medical device for medical purposes. By the term "medical device for electromagnetic tracking", it is meant to provide a medical device for medical purposes, which medical device is suitable for electromagnetic tracking.

Advantageously, the electromagnetic tracking allows the determination of the positioning of the medical device in the spatial situation, for example in an operational theatre, for example in a hospital. By providing the wireless readout unit to be attached to the medical device, it is possible to pre-process the data provided by the electromagnetic tracking sensor and then to transfer the pre-processed data to a control unit of a larger system.

According to an example, an interface is provided to temporarily attach the wireless readout unit to the body portion.

Advantageously, this allows the detachment of the wireless readout unit and an easy connection of the wireless readout unit to the body portion, i.e. the actual medical device.

According to an example, the medical device is a catheter having an elongate body and a grip portion. The electromagnetic tracking sensor is arranged at a distal end portion of the elongate body and the wireless readout unit is attached to the grip portion.

Advantageously, a catheter is provided that can be used for electromagnetic tracking, due to the positioning of the sensor at a tip portion or distal end portion. The integration of the wireless readout unit in the area of the grip portion allows an easy handling.

According to another example, the medical device is an ultrasound probe with a transducer head portion. The electromagnetic tracking sensor and the wireless readout unit are attached to the ultrasound probe. In an example, the electromagnetic tracking sensor and the wireless readout unit are arranged at the head portion.

Advantageously, it is possible to track the ultrasound probe in view of the spatial situation or spatial arrangement in the operational theatre. Hence, it is for example possible to allow a registration of the image data acquired by the ultrasound probe in relation with a patient, if such patient is registered within a global coordinate system. For example, different image data of the same patient can be registered with the tracking data.

According to a third aspect, an electromagnetic tracking system of medical devices is provided. The system comprises a field generator for generating an electromagnetic field with a known spatial distribution in a region of interest. Further, a control unit is provided. Still further, at least one medical device for electromagnetic tracking according to one of the above-mentioned examples is provided. The control unit is configured to control the generation of the electromagnetic field by the field generator, and to receive signals from the wireless readout unit.

Advantageously, an electromagnetic tracking system is provided with reduced data communication, or with improved data via the wireless links due to the use of the wireless readout unit pre-processing the data to be transmitted via the wireless link.

In an example, for the identification of electromagnetic sources, it is provided that the identification and separation of the different signal components related to the various field generating elements is linked to how the field generator is controlled.

According to an example, upon activation, the control unit provides electromagnetic field data to the data processor of the wireless readout unit.

This advantageously allows a respective pre-processing also considering such field data.

According to an example, the wireless readout unit and the control unit (or processing unit) are configured to be synchronized so that the wireless unit can isolate the signal components from the different field generating elements.

According to a fourth aspect, a method for tracking of medical devices is provided. The method comprising the following steps:

a) generating an electromagnetic field;
b) measuring an intensity of the electromagnetic field by a sensor attached to a predetermined point of a medical device and providing raw signals to a wireless readout unit that is at least temporarily attached to the medical device;
c) pre-processing the raw signals by the wireless readout unit;
d) transmitting the pre-processed data to a control unit of an electromagnetic tracking system by a wireless data link; and
e) determining a spatial position and/or spatial orientation of the predetermined point of the medical device; and wherein in step c), for the pre-processing of the raw signals the data processor is configured to perform:

identification and/or separation of different signal components induced by different field emitting elements of the field generator; and/or extraction of signal components or signal parameters used for triangulation.

In an example, the step e) comprises the determination of the spatial position. In another example, the step e) comprises the determination of the spatial orientation. In a still further example, the step e) comprises the determination of the spatial position and the spatial orientation.

According to an aspect, for spatial tracking of a medical device, a wireless readout unit is provided that receives data from an electromagnetic sensor. Before transmitting data via a wireless data link to a control unit of an overall electromagnetic tracking system, the wireless readout unit provides at least a part of the functions of the control unit, by implementing a pre-processing of the data provided by the electromagnetic sensor. Hence, pre-processed data is sent via the wireless link to a control unit, thus facilitating and improving the data link connection of an electromagnetic tracking system.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 4 shows a catheter as an example of a medical device for electromagnetic tracking in relation with a wireless readout unit provided as a dongle, wherein FIG. 4A shows the detached state and FIG. 4B shows the attached state.

DETAILED DESCRIPTION OF EMBODIMENTS

Figure 1:
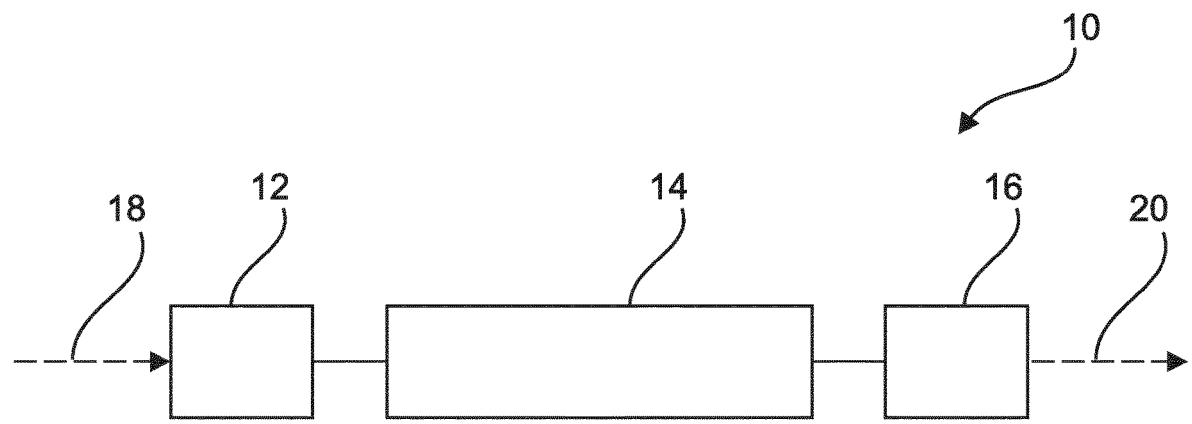
FIG. 1 shows an example of a wireless readout unit for an electromagnetic tracking system of medical devices.
Figure 3:
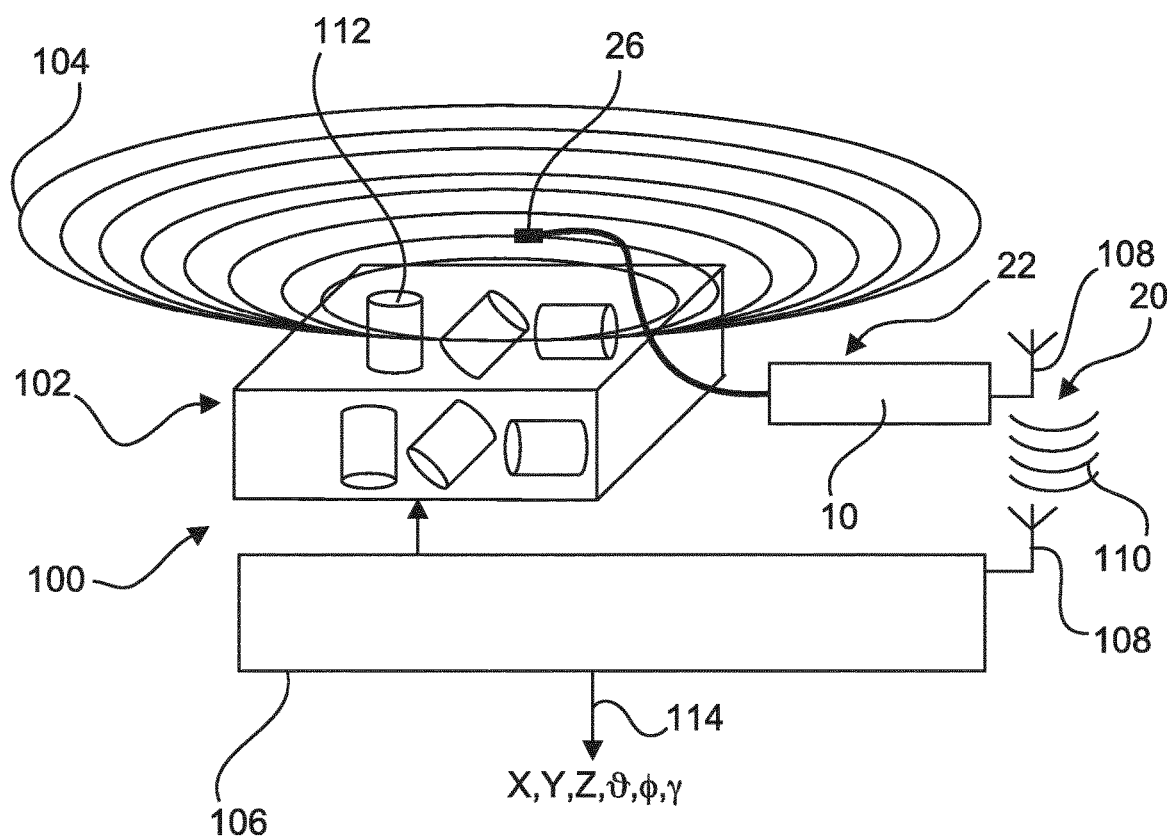
FIG. 3 shows an example of an electromagnetic tracking system of medical devices in a schematic setup.

FIG. 1 shows a wireless readout unit 10 for an electromagnetic tracking system of medical devices (for the system, see also FIG. 3). The wireless readout unit 10 comprises a data input 12, a data processor 14 and a data output 16. The data input 12 is configured to receive raw signals 18, indicated with a hashed arrow, from an electromagnetic sensor (not shown). The data processor 14 is configured to at least partly pre-process the raw signals 18 provided by the data input 12 for further transformation. The data output 16 is configured for data transmission of the at least partly pre-processed data to a control unit of an electromagnetic tracking system of medical devices.

The data output 16 provides a wireless data link 20, indicated with a further hashed arrow, to a control unit (not further shown) of an electromagnetic tracking system of medical devices. The wireless link may also be provided to a processing unit or console.

Figure 2:
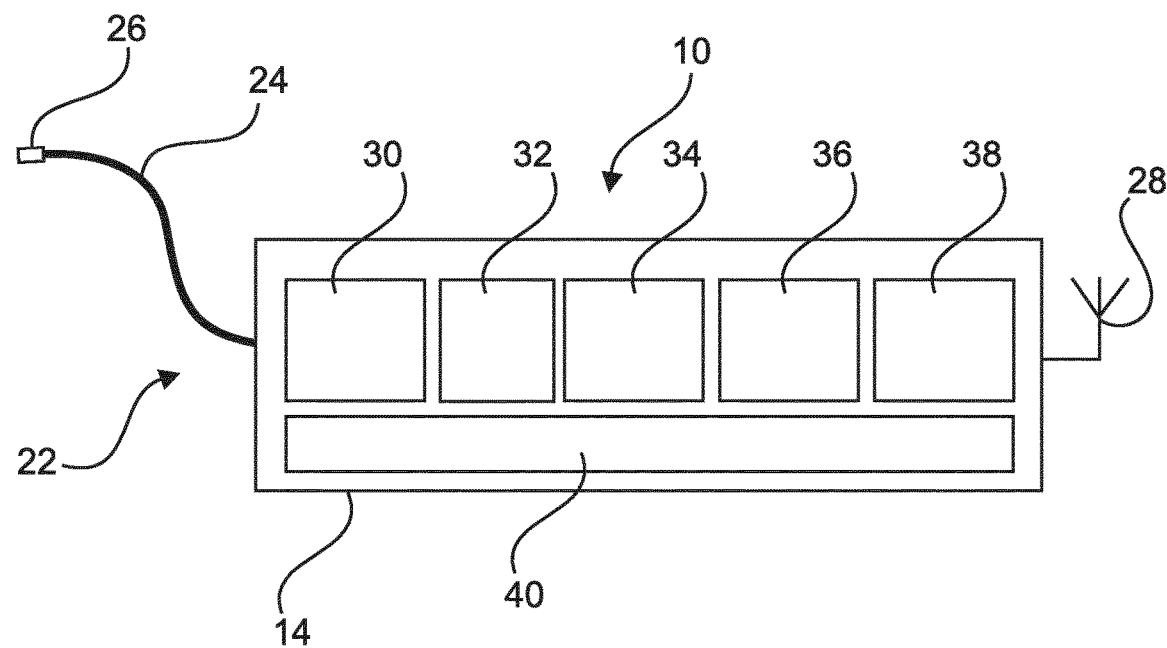
FIG. 2 shows an example of a medical device for electromagnetic tracking in a schematic setup.

FIG. 2 shows an example of a medical device 22 for electromagnetic tracking. The device comprises at least a body portion 24 and an electromagnetic tracking sensor 26. Further, at least one example of the wireless readout unit 10 according to one of the above-mentioned, and below-mentioned, examples is provided. The electromagnetic tracking sensor 26 is configured to measure an intensity of an electromagnetic field generated by a field generator (see also FIG. 3) of an electromagnetic tracking system of medical devices. The electromagnetic tracking sensor 26 is fixedly attached to a determination part of the medical device 22. The wireless readout unit 10 is at least temporarily attached to the body portion 24.

Before further describing the wireless readout unit 10 and the provided pre-processing of the raw signals, it is briefly referred to the medical device 22.

The medical device 22 is provided for interventional or diagnostic tasks, i.e. to perform a medical function. The electromagnetic tracking is an addition to the medical device and used to monitor the position and possibly orientation of the medical device or of a portion of the medical device.

In an example, for the state information of the device, it is provided that the electromagnetic tracking system is provided with an additional two-way communication with a device, which device can be used to implement for example buttons or status LEDs. The wireless link may be able to relay this information as well. This type of information may span only a few bits per device and may not require processing. It can thus be easily performed once a connection has been established.

In an example, for the integration with a device to be tracked, it is provided that the wireless readout unit is a reusable standalone device that plugs into the device to be tracked as a dongle (see also below). A connection to the sensor is provided and, if applicable, a connection to the energy source of the device to be tracked. This is particularly appealing for low cost or disposable devices and for devices that might not always require the use of tracking. For example, a catheter for cardio-vascular applications is provided. In an alternative example, the wireless readout unit is permanently integrated within the device to be tracked. This scenario is appealing for reusable medical devices that are expected to make use of the tracking functionality most of the time. For example, a tracked US (ultrasound) transducer is provided. Referring back to FIG. 1, it is noted that the data input 12 and the data output 16 are not further illustrated in FIG. 2, but are of course provided.

In FIG. 2, an antenna symbol 28 indicates the provided wireless data link 20 to a control unit.

The wireless readout unit 10 is locally performing at least some of the functions of a control unit. In an example, the wireless readout unit sends the results to the control unit for the triangulation of the device location. In another example, the triangulation of the device location is provided at least partly by the wireless readout unit.

In an example, for the wireless link 20, it is provided that the wireless link allows real time operation and supports tracking multiple devices simultaneously. In addition, to limit interference with/from other devices, in an example, dedicated wireless channels in an operational theatre (hospital) environment are used. The ability of locally identifying and separating the signal components related to the different field generating elements (coils) and extracting features from these components, can significantly reduce the bandwidth and synchronization requirements of the radio, i.e., wireless, link. It is also possible to provide the wireless link as a temporal link, which sends data only in predetermined timeslots. For example, feature extraction is locally performed and the radio (wireless link) transmits only the features that are calculated for each localization event (frame) that will then be used to determine the location of the sensor at the time of calculation. This may offer further improved reliability of the tracking system.

In an example, the whole processing and communication chain has a predictable and sufficiently low latency so that it would allow for proper hand-eye coordination required for the application of this example during medical interventions.

With reference to FIG. 1, in the following, the data processor 14 is further described, referring to the illustration of FIG. 2 concerning the data processor 14.

For the pre-processing of the raw signals 18, the data processor 14 is configured to perform at least one of the group of filtering of the raw signals, amplification of the raw signals, analogue processing and analogue-to-digital conversion of the signals, or identification and/or separation of different signal components induced by different field emitting elements of the field generator, and extraction of signal components or signal parameters that can be used for triangulation.

According to an example, shown in FIG. 2 as separate options, that can be used individually or in combination of various kinds, the data processor 14 comprises an amplification and/or filtering segment 30. Further, an analogue-digital conversion segment 32 may be provided. Still further, an identification segment 34 for identifying electromagnetic sources and their respective ID is provided. Further, a feature extraction segment 36 may be provided. Still further, a radio, i.e. wireless data link segment 38 indicates the respective conversion of the data for the wireless link 20.

The segments can be provided as sub-portions of a common processor, or as individual circuits. In an example, the wireless readout unit takes over from the control unit of an electromagnetic tracking system (shown in FIG. 3) some of the functionality, for example some of its most basic functionality. The wireless control unit may be able to perform, as indicated above:

i) Filtering, amplifying and performing analogue processing and analogue-to-digital conversion of the sensor signal;
ii) Identifying and separating the different signal components induced by the different field emitting elements (coils) of the field generator;
iii) Extracting from the mentioned signal components all the features (e.g. signal component amplitude) that are used by the control unit to perform the triangulation; and
iv) Communicating the mentioned features to the control unit via the wireless link.

In an example, for the amplification and filtering it is provided that the signal from the sensor is filtered to remove unwanted noise/interference and then amplified. For example, the signal is digitized for a more generalized processing, but in another example, an analogue-to-digital conversion is provided.

In a further example, indicated in FIG. 2 as an option, the wireless readout unit 10 further comprises a local energy source 40. The energy source is configured to supply electric energy to the wireless readout unit 10.

In an example, the wireless readout unit 10 is supplied with electric energy by an energy source of a medical device that is to be tracked, i.e. the wireless readout unit 10 receives power from an existing power source of the medical device it is attached to, e.g. the same power source that powers an ultrasound probe or power from an RF (radio frequency) generator in an ablation catheter.

In an example, for the energy source, it is provided a battery that is part of the wireless readout unit.

In an alternative example, a connection to the medical device to be tracked is provided, for example, if this is an electrically powered medical device such as an ultrasound transducer, the wireless readout unit could be configured to be supplied of energy by the medical device itself. Another example provides a combination of a wireless readout unit containing a battery, but that is also using an external power source if connected to a powered device.

In another example, the data processor is further configured to determine a change of the raw signals in relation to a given threshold, and the data transmission is only activated in case the change is above the threshold.

FIG. 3 shows an electromagnetic system 100 of medical devices. The system comprises a field generator 102 for generating an electromagnetic field with a known spatial distribution in a region of interest. The electromagnetic field is indicated with lines 104. Further, a control unit 106 is provided. Still further, at least one example of the medical device 22 for electromagnetic tracking according to one of the above-mentioned examples is provided. The control unit 106 is configured to control the generation of the electromagnetic field by the field generator 102, and to receive signals from the wireless readout unit 10.

The communication via the wireless data link 20 is indicated with two antenna symbols 108 and respective data wave lines 110.

The field generator 102 may comprise a plurality of coils 112 that can generate different electromagnetic field segments to allow a tracking of the electromagnetic sensor 26 in a spatial manner.

An output arrow 114 of the control unit 106 indicates the result of the spatial tracking of the electromagnetic sensor 26 of the medical device 22.

It must be noted that the field generator 102 is schematically shown with a square box enclosing the plurality of coils 112 for illustration purposes only. Of course, the coils 112 may be distributed within the space, in which the electromagnetic tracking takes place.

Hence, in an example, the field generator comprises a set of coils arranged in different positions and orientations, as indicated by the coils 112 in FIG. 3. The field generator 102 thus generates an electromagnetic (EM) field with a known, and often calibrated, spatial distribution in the region of interest. An instrument, like the medical device, for example a catheter, can be equipped with the electromagnetic sensor 26, e.g. a simple coil that can measure the intensity of the electromagnetic field generated by the field generator. This measure, i.e. this so-to-speak raw signal, or raw data, is then interpreted together with the knowledge of the spatial distribution of the generated field in order to estimate the coordinates and orientation of the electromagnetic sensor and therefore of the device, in which the sensor is embedded (or typically of a part of the device that is particularly relevant, such as the tip of a catheter).

In an example, the control unit 106 is able to interpret the information packets received by the wireless readout unit(s) 10 in order to perform location triangulation. In another example, it is provided to perform the location triangulation in the wireless readout unit 10 itself. In this example, electromagnetic field generator calibration is provided to the wireless readout unit 10.

In an example, the control unit 106 is configured to perform (calculate) a triangulation for determining a location of the electromagnetic tracking sensor of the medical device.

In an example, more than one medical device are provided, for example two, three, four, five, six, seven, eight, nine or ten medical devices, or more than ten medical devices.

For the identification of electromagnetic sources within the wireless readout element, it is provided that the identification and separation of the different signal components related to the various field generating elements is linked to how the field generator is controlled.

For example, it is provided:

Frequency division: If the different coils are generating electromagnetic signals with spectra that are separated in the frequency domain, the identification of the different signal components could be as straight forward as applying frequency based filtering to isolate the different components.

Time division: If the different coils are activated one at a time in a time division fashion, identifying the different components requires achieving the proper synchronization between the readout interface and the activation sequence. This could be achieved in different ways:

The control unit sends, via a wireless link, a beacon signal that can be used to synchronize the signal detection with the sequence of activation of the various coils.

The communication protocol between control unit and wireless readout unit guarantees sufficient time synchronization between them.

The control unit activates the coils following a protocol that enables self-synchronization of the read out units. Examples include: i) The control unit introduces a recognizable "start of sequence" signal between repetitions of the measurement sequence (for example a known sequence of alternating periods of time, in which all the coils are simultaneously active or simultaneously inactive), ii) The phase of the electromagnetic signals changes between subsequent repetitions of the sequence so that the transition can be easily detected, iii) The frequency of the electromagnetic signals changes between subsequent repetitions of the sequence so that the transition can be easily detected.

In an example, for the feature extraction it is provided that, in order to limit the bandwidth requirement of the wireless link, as indicated above, the wireless readout unit does not send raw data from the sensor to the control unit, but extracts only the relevant features that should be used for the triangulation of the location. An example of these features is the signal power received from the various coils of the field generator.

In an example, the control unit calculates coordinates based on the sensor data. The control unit also regulates, i.e. controls, the generation of the electromagnetic field, which provides the basis for the electromagnetic tracking system 100 since the electromagnetic field causes the electromagnetic sensor 26 to provide the raw signals. The control unit 106 can also be referred to as a processing unit, or main processing unit.

In an example, feature extraction is performed after the identification of the signal components so that the wireless readout unit 10 can create a packet of information containing all the features correctly related to the various electromagnetic sources for a given localization frame. This packet could include a frame number (or a time-stamp). Following this approach, the control unit 106 can always calculate a proper device location for each information packet correctly received (all the information required is part of a single packet in an example) and it will be able to identify missing packets.

According to an example, provided as an option, upon activation, the control unit 106 provides electromagnetic field data to the data processor 14 of the wireless readout unit 10 (not further shown in detail in FIG. 3).

In a further option, the wireless link 20 is configured as a temporal link connecting the wireless readout unit 10 and the control unit 106 in predetermined timeslots.

In an example, the wireless readout unit is provided as a detachable dongle 42 to be temporarily attached to a medical device.

Figure 4:
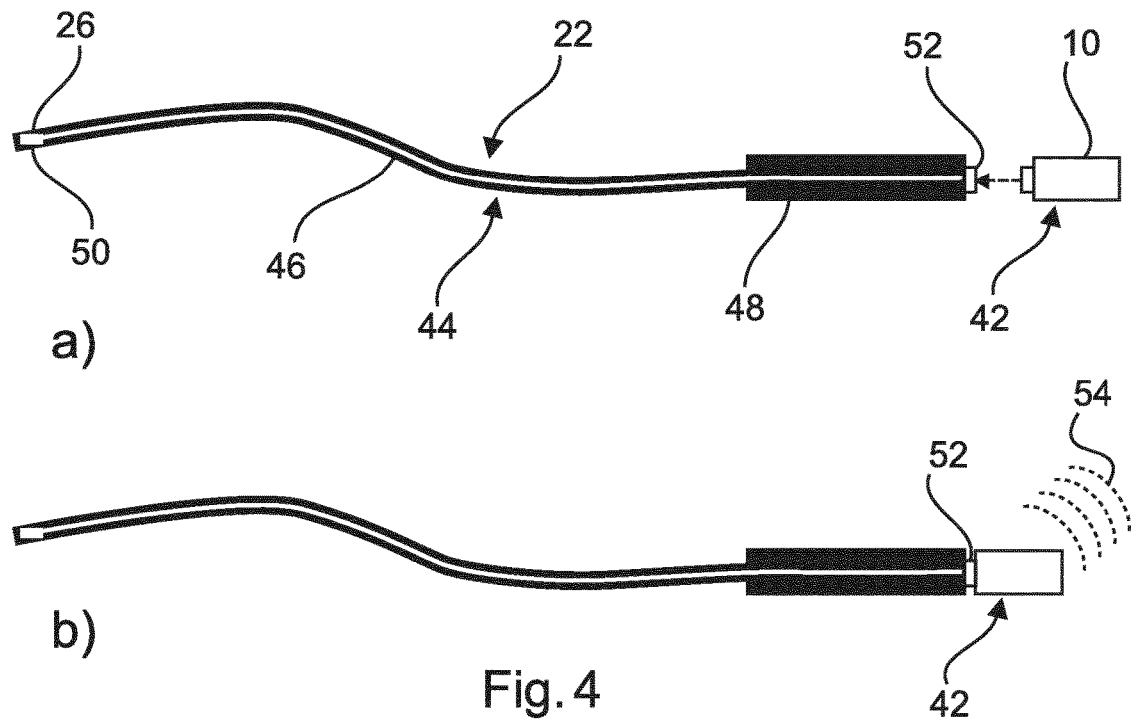

FIG. 4 shows an example of the medical device 22 in form of a catheter 44. The catheter 44 has an elongate body 46 and a grip portion 48. The electromagnetic tracking sensor 26 is arranged at a distal end portion 50 of the elongate body 46. The wireless readout unit 10 is attached to the grip portion 48.

For example, an interface 52 is provided to temporarily attach the wireless readout unit 10 to the body portion 24 of the medical device. For example, the grip portion 48 can be considered as a body portion.

FIG. 4A shows the state, in which the medical device 22 is about to be connected to the dongle 42. FIG. 4B shows the state, in which the dongle 42 is connected to the medical device via the interface 52. Radiation waves shown in hashed lines 54 indicate hence the functioning of the electromagnetic tracking, once the dongle is attached.

This allows the use of a small number of dongles, for example one or more dongles, to a large number of devices that can then be tracked by electromagnetic tracking. This may be of advantage for disposable devices. The dongle can be used for multiple interventions, while the devices may be disposed after every use.

Figure 5:
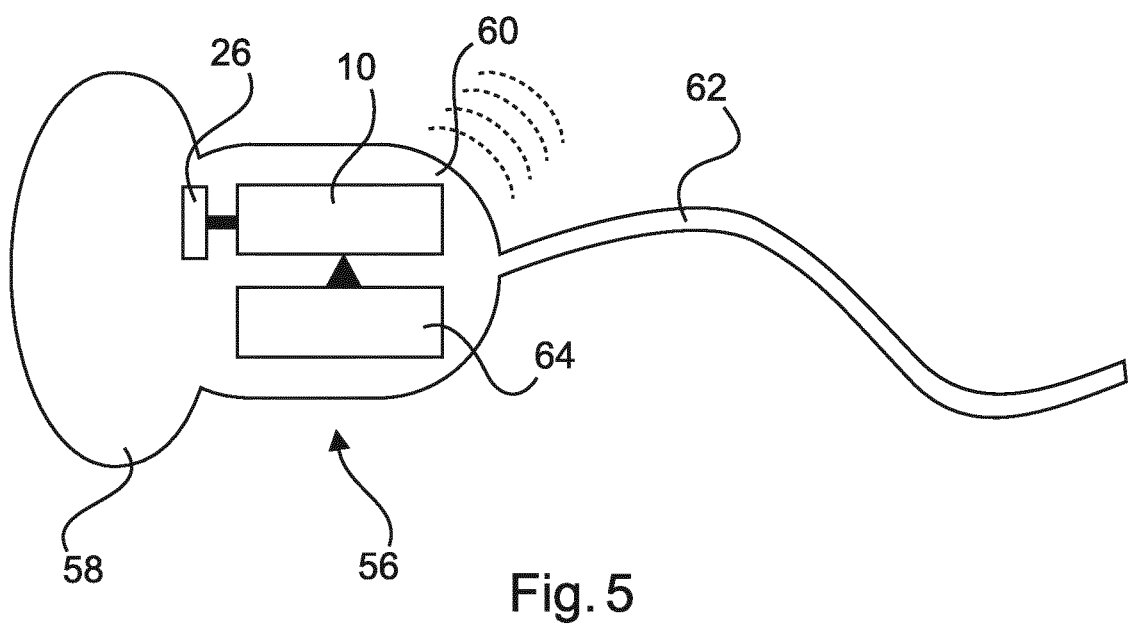
FIG. 5 shows an ultrasound probe as an example of a medical device, which ultrasound probe can be used for electromagnetic tracking.

FIG. 5 shows a further example of the medical device 10 in form of an ultrasound probe 56 in a schematic setup. The ultrasound probe 56 has a transducer head portion 58 and the electromagnetic tracking sensor 26 and the wireless readout unit 10 are arranged at the head portion 58. The head portion 58 may also comprise a handle (sub-) portion, or sub-portion 60, and the electromagnetic tracking sensor 26 is attached to the ultrasound probe 56. For example, the wireless readout unit 10 and the electromagnetic tracking sensor 26 can be provided in the front head portion and the wireless readout unit 10 can be arranged within the handle or grip sub-portion. In an example, the wireless readout unit 10 and the electromagnetic tracking sensor 26 are attached to different locations, as long as the device is sufficiently rigid.

The ultrasound probe 56 can be operated by a separate or external energy supply, as indicated with cable 62, but may also be provided with an energy storage within the ultrasound probe 56, i.e. without the cable connection 62 and hence with an integrated energy supply. Hence, an energy or power supply 64 of the ultrasound probe can also be used for operating the wireless readout unit 10.

Figure 6:
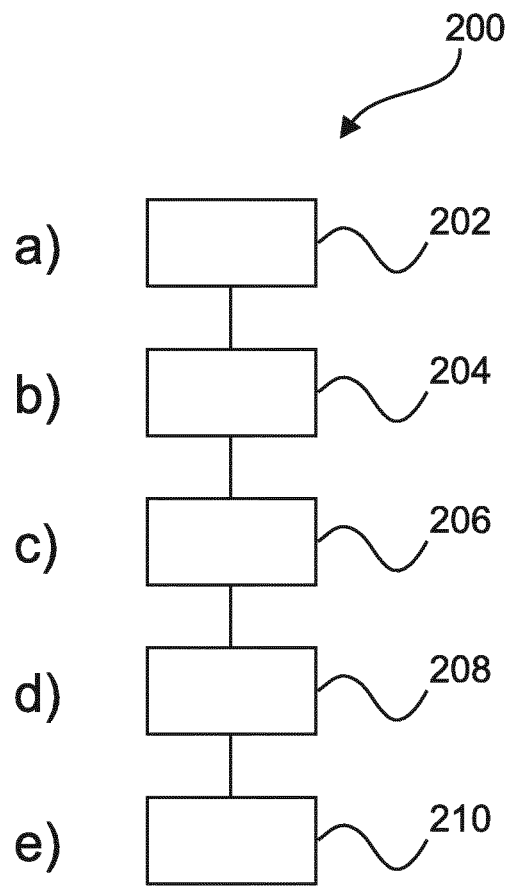
FIG. 6 shows basic steps of an example of a method for tracking of medical devices.

FIG. 6 shows an example of a method 200 for tracking of medical devices. The following steps are provided: In a first step 202, also referred to as step a), an electromagnetic field is generated. In a second step 204, also referred to as step b), an intensity of the electromagnetic field is measured by a sensor attached to a predetermined point of a medical device, and raw signals are provided to a wireless readout unit that is at least temporarily attached to the medical device. In a third step 206, also referred to as step c), the raw signals are pre-processed by the wireless readout unit. In a fourth step 208, also referred to as step d), the pre-processed data is transmitted to a control unit of an electromagnetic tracking system by a wireless data link. In a fifth step 210, also referred to as step e), a spatial position and/or spatial orientation of the predetermined point of the medical device is determined. Hence, the medical device can be tracked in an improved manner.

It has to be noted that embodiments of the invention are described with reference to different subject matters. In particular, some embodiments are described with reference to an insert whereas other embodiments are described with reference to the apparatus. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A wireless readout device for an electromagnetic tracking system of medical devices, the wireless readout device comprising:
   a data input configured to receive raw signals from an electromagnetic sensor of a medical device;
   wireless communication circuitry configured to communicate wirelessly over a wireless link with a control circuit of the electromagnetic tracking system, wherein the electromagnetic tracking system comprises an electromagnetic field generator having a plurality of field emitting elements; and
   data pre-processing circuitry configured to at least partly pre-process the raw signals provided by the data input by:
      identifying different signal components induced by different field emitting elements of the electromagnetic field generator;

extracting signal components corresponding to the different field emitting elements of the electromagnetic field generator; and performing a calculation that at least partly provides triangulation of a location of the medical device based on the extracted signal components, wherein the wireless communication circuitry is configured to communicate the pre-processed data to the control circuit of the electromagnetic tracking system, wherein the wireless readout device is provided as a detachable dongle to be temporarily attached to the medical device.

2. The wireless readout device according to claim 1, wherein the data pre-processing circuitry is further configured to perform at least one of:
filter of the raw signals;
amplification of the raw signals; and
analogue processing and analogue-to-digital conversion of the signals.

3. The wireless readout device according to claim 1, further comprising:
a local energy source;
wherein the local energy source is configured to supply electric energy to the wireless readout device.

4. The wireless readout device according to claim 1, wherein the wireless readout device is supplied with electric energy by an energy source of a medical device that is to be tracked.

5. A medical device for electromagnetic tracking, the medical device comprising:
at least a body portion;
an electromagnetic tracking sensor; and
the wireless readout device according to claim 1;
wherein the electromagnetic tracking sensor is configured to measure an intensity of an electromagnetic field generated by a field generator;
wherein the electromagnetic tracking sensor is fixedly attached to a determined part of the medical device; and
wherein the wireless readout device is at least temporarily attached to the body portion.

6. The medical device according to claim 5, wherein an interface is provided to temporarily attach the wireless readout device to the body portion.

7. The medical device according to claim 5, wherein the medical device is a catheter having an elongate body and a grip portion;
wherein the electromagnetic tracking sensor is arranged at a distal end portion of the elongate body; and
wherein the wireless readout device is attached to the grip portion.

8. The medical device according to claim 5, wherein the medical device is an ultrasound probe with a transducer head portion; and
wherein the electromagnetic tracking sensor and the wireless readout device are attached to the ultrasound probe.

9. An electromagnetic tracking system of medical devices, the electromagnetic tracking system comprising:
a field generator for generating an electromagnetic field with a known spatial distribution in a region of interest; and
at least one medical device for electromagnetic tracking according to claim 5;
wherein the control circuit is configured to control the generation of the electromagnetic field by the field generator, and to receive signals from the wireless readout device.

10. The electromagnetic tracking system according to claim 9, wherein upon activation, the control circuit provides electromagnetic field data to the the data pre-processing circuitry of the wireless readout device.

11. The electromagnetic tracking system according to claim 9, wherein for the identification of electromagnetic sources, it is provided that the identification and separation of the different signal components related to the plurality of field emitting elements is linked to how the field generator is controlled.

12. The electromagnetic tracking system according to claim 9, wherein the wireless link is configured as a temporal link connecting the wireless readout device and the control unit in predetermined timeslots.

13. A method for tracking of medical devices, said method comprising the following steps:
a) generating an electromagnetic field with a field generator;
b) measuring an intensity of the electromagnetic field by a sensor attached to a predetermined point of a medical device and providing raw signals to a wireless readout device including a data processor and provided as a detachable dongle that is at least temporarily attached to the medical device;
c) pre-processing the raw signals by the wireless readout device;
d) transmitting the pre-processed data to a control circuit of an electromagnetic tracking system by a wireless data link;
determining at least one of a spatial position and a spatial orientation of the predetermined point of the medical device; and
wherein in step c), for the pre-processing of the raw signals, the data processor is configured to perform:
an identification of different signal components induced by different field emitting elements of the field generator;
an extraction of signal components; and
a calculation that at least partly provides triangulation of a location of the medical device based on the extracted signal components.

* * * * *